United States Patent
Lardinois et al.

(10) Patent No.: US 7,214,795 B2
(45) Date of Patent: May 8, 2007

(54) PROCESS FOR PREPARING MELAMINE

(75) Inventors: Guillaume Mario Hubert Jozef Lardinois, Elsloo (NL); Fredericus Henricus Maria Buitink, Grathem (NL)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 10/503,230

(22) PCT Filed: Feb. 6, 2003

(86) PCT No.: PCT/NL03/00082

§ 371 (c)(1),
(2), (4) Date: Apr. 4, 2005

(87) PCT Pub. No.: WO03/066605

PCT Pub. Date: Aug. 14, 2003

(65) Prior Publication Data

US 2005/0165230 A1  Jul. 28, 2005

(30) Foreign Application Priority Data

Feb. 7, 2002  (NL) .................................... 1019913

(51) Int. Cl.
*C07D 251/60* (2006.01)
(52) U.S. Cl. ..................................... 544/201; 544/203

(58) Field of Classification Search ................ 544/201, 544/203

See application file for complete search history.

(56) References Cited

U.S. PATENT DOCUMENTS 5,384,404 A  1/1995  Lee

FOREIGN PATENT DOCUMENTS

| WO | 96 20933 | 7/1996 |
| WO | 01 56999 | 8/2001 |
| WO | 02 14289 | 2/2002 |

*Primary Examiner*—Venkataraman Balasubramanian
(74) *Attorney, Agent, or Firm*—Nixon & Vanderhye, PC

(57) ABSTRACT

The invention relates to a process for preparing melamine, comprising a cooling step from which a mixture $H_2O$ containing $NH_3$, $CO_2$ and $H_2O$ is released, wherein:

the mixture and a flow of liquid $NH_3$ are fed to an absorption section;

the mixture and the flow of liquid $NH_3$ in the absorption section are contacted with each other, with gaseous $NH_3$ and an ammonium carbamate solution being formed;

the gaseous $NH_3$ and the ammonium carbamate solution are separately discharged from the absorption section, wherein a part of the discharged ammonium carbamate solution is returned to the cooling step and a part of the removed gaseous $NH_3$ is liquefied and returned to the absorption section.

13 Claims, 5 Drawing Sheets

PROCESS FOR PREPARING MELAMINE

CROSS REFERENCE TO RELATED APPLICATION

This application is the National Phase of International Application PCT/NL03/00082 filed Feb. 6, 2003 which designated the U.S., and was published in the English language.

FIELD OF INVENTION

The invention relates to a process for preparing melamine, comprising a first cooling step from which a mixture containing $NH_3$, $CO_2$ and $H_2O$ is released, wherein:
the mixture and a flow of liquid $NH_3$ are fed to an absorption section;
the mixture and the flow of liquid $NH_3$ in the absorption section are contacted with each other, with gaseous $NH_3$ and an ammonium carbamate solution being formed;
the gaseous $NH_3$ and the ammonium carbamate solution are separately discharged from the absorption section.

BACKGROUND AND SUMMARY OF THE INVENTION

A process of the same kind is known from "Melamine and Guanamines", section 4.1.3 of Ullmann's Encyclopedia of Industrial Chemistry, Sixth Edition, 2001 Electronic Release. Furthermore, in the known process, the mixture, prior to being supplied to the absorption section, is subjected to a partial condensation step.

The mixture in the known process contains, as mentioned above, $NH_3$, $CO_2$ and $H_2O$. The $CO_2$ and a part of the $NH_3$ in the mixture mainly originate from the reaction of urea to form melamine, which proceeds as follows:

$$6\ CO(NH_2)_2 \longrightarrow C_3N_6H_6 + 6NH_3 + 3CO_2$$

Usually $NH_3$ is used as fluisidation gas and atomizing gas during the melamine synthesis, which may also cause $NH_3$ to enter the mixture. Fluidization gas serves to keep the synthesis catalyst in a fluid state. Atomizing gas serves to atomize the urea in the synthesis reactor. The $H_2O$ in the mixture mainly originates from the first cooling step, where an aqueous flow is used as a cooling medium for the reaction product; here the $H_2O$ partly evaporates.

The aforementioned known absorption section, which is designed as a column, is intended amongst other things to separate a flow of gaseous $NH_3$ from the mixture and discharge it from the absorption section. The discharged flow of gaseous $NH_3$ is removed and generally returned to a melamine synthesis reactor to serve there as a fluidization gas and/or atomizing gas. A part of the gaseous $NH_3$ is passed through a scrubber, whose object it is to to separate and discharge so-called inert compounds such as $H_2$ and $N_2$.

The known absorption section is also intended to form, from $NH_3$ and from virtually all $CO_2$ and $H_2O$ from the mixture, an ammonium carbamate solution and discharge that solution. The discharged ammonium carbamate solution is removed, after which generally in downstream steps the $CO_2$ and the $NH_3$ are liberated from the discharged ammonium carbamate solution, either as such or in the form of an ammonium carbamate solution with a considerably reduced water content, in which process a practically pure flow of water is released which in general is a waste stream and is discharged. As is known, the urea synthesis efficiency decreases as the quantity of water in the raw materials increases. The liberated $CO_2$ and a part of the liberated $NH_3$, as such or in the form of an ammonium carbamate solution with a considerably reduced water content, can serve as a raw material for the production of urea or for the production of ammonium nitrate or ammonium sulfate. The remaining part of the liberated $NH_3$ is liquefied in the known process and recirculated to the absorption section as part of the flow of liquid $NH_3$.

A disadvantage of the known process is that the recovery of the $NH_3$ to be recirculated to the absorption section from the ammonium carbamate solution requires a great deal of energy, for example in the form of steam.

The object of the invention is to reduce the energy consumption in the downstream steps that are applied to the discharged ammonium carbamate solution.

The said object is achieved in that a part of the discharged ammonium carbamate solution is returned to the first cooling step and a part of the discharged gaseous $NH_3$ is liquefied in a second cooling step and returned to the absorption section.

The process according to the invention ensures that less $NH_3$ is removed via the ammonium carbamate solution per unit time than in the known process. As a result, the quantity of $NH_3$ which is liberated in the downstream steps for recirculation to the absorption section can decrease, which yields an energy saving, for example in steam consumption. A further advantage of the process according to the invention is that less $H_2O$ is removed per unit time via the ammonium carbamate solution than in the known process. This allows a decrease in the liquid load of the equipment items in which the downstream steps are carried out for liberating the $CO_2$ and the $NH_3$ from the removed ammonium carbamate solution, for example for the preparation of urea. As a result said downstream steps can be carried out in smaller equipment items and with less energy consumption than in the known process, which is cheaper.

The process according to the invention comprises a first cooling step for cooling an essentially gaseous flow originating from a melamine synthesis reactor and containing essentially melamine, $NH_3$ and $CO_2$. The flow from the melamine synthesis reactor is contacted with a coolant. The coolant comprises a flow consisting essentially of an ammonium carbamate solution to be discussed later. The coolant comprises in addition generally also a flow essentially consisting of water; for this purpose use is usually made of an aqueous flow originating from a recovery section. The coolant flows can be supplied separately or jointly to the first cooling step. As the flow from the melamine synthesis reactor is contacted with the coolant there evolve a solution (containing dissolved melamine in an aqueous phase) or a slurry (containing melamine crystals in an aqueous phase) and a generally gaseous mixture containing $NH_3$, $CO_2$ and $H_2O$. The solution or the slurry is discharged from the first cooling step and fed to a recovery section in which melamine crystals are formed (if necessary) and separated. The said mixture is usually gaseous and usually contains more than 40 wt % $NH_3$, less than 50 wt % $CO_2$ and less than 40 wt % $H_2O$ at a pressure usually between 0.1 MPa and 4 MPa, and is fed to an absorption section. In addition a flow of liquid $NH_3$ is also fed to the absorption section. The percentages stated here and hereafter are percentages by weight, unless otherwise indicated.

In the absorption section according to the invention the mixture is contacted with the flow of liquid $NH_3$. This gives rise to a flow of gaseous $NH_3$ and virtually all $CO_2$ and $H_2O$ go into the liquid phase. To facilitate the transition of $CO_2$ into the liquid phase, an additional flow consisting essentially of water may be fed to the absorption section. The required quantities of the flow of liquid $NH_3$ and of the additional flow consisting essentially of water that are fed to the absorption section are largely determined by the desired purity of the discharged flow of gaseous $NH_3$. Usually a purity of 99% or higher is desired. The higher the desired purity of the discharged gaseous $NH_3$, the larger the required quantities of the flow of liquid $NH_3$ and of the additional flow consisting essentially of water.

The flow of gaseous $NH_3$, consisting essentially of $NH_3$ and which in addition may contain up to approximately 1 wt % of other compounds such as $CO_2$, $H_2O$, $N_2$ and $H_2$, is discharged from the absorption section. In the process according to the invention a part of the discharged gaseous $NH_3$ is liquefied in the second cooling step and returned to the absorption section; the remaining part is removed and, as previously indicated, usually used as fluidization gas and/or atomizing gas in the melamine synthesis reactor. It is an advantage of the process according to the invention that the gaseous $NH_3$ can be used directly as fluidization gas an/or atomising gas, without the need of an evaporating step as is the case when the $NH_3$ to be used is supplied in liquid form. Liquefaction in the second cooling step may be accomplished by means known per se, such as for example by means of a heat exchanger. An advantage of the process according to the invention is that the quantity of fresh liquid $NH_3$ to be fed to the absorption section can decrease, because a flow of liquid $NH_3$ is already available. A further advantage of the process according to the invention is that inert compounds such as for example $N_2$ and $H_2$, which cannot be easily liquefied because their condensation temperature is much lower than that of $NH_3$, can readily be separated from the liquefied $NH_3$ and removed as an inert gaseous vent stream. The inert vent stream will in general still contain a residual quantity of $NH_3$. If it is desired to remove this residual quantity of $NH_3$ the inert vent stream can be passed through a scrubber, which can however be significantly smaller than the aforementioned scrubber in the known process.

The liquid phase formed in and discharged from the absorption section consists essentially of an ammonium carbamate solution. By this is meant a solution of ammonium carbamate in water, which in addition may contain other compounds such as free dissolved $NH_3$, free dissolved $CO_2$ and ammonium bicarbonate. In the process according to the invention a part of the discharged ammonium carbamate solution is returned to the first cooling step; the remaining part is removed. The returned ammonium carbamate solution serves as a coolant in the first cooling step, will largely evaporate into $NH_3$, $CO_2$ and $H_2O$ and will thus be absorbed in the mixture which is released in the first cooling step and is fed to the absorption section; in this way there is formed in the process according to the invention a circulation flow between the first cooling step and the absorption section.

The removed ammonium carbamate solution is generally the most important medium for removing the $CO_2$ evolving in the urea-to-melamine reaction. As a result, the quantity of $CO_2$, as such or as an ion, in the removed ammonium carbamate solution is usually an important control parameter for operating an absorption section in a process for the preparation of melamine and also for operating the absorption section according to the invention. The part of the discharged ammonium carbamate solution that is returned to the first cooling step is determined preferably in relation to the quantity of $CO_2$ that is present in the removed ammonium carbamate solution either as such or as an ion. The quantity of $CO_2$ in the removed ammonium carbamate solution is hereinafter referred to as removed $CO_2$. The quantity by weight of ammonium carbamate solution which is returned to the first cooling step divided by the quantity by weight of removed $CO_2$ is preferably between 0.01 and 5, more preferably between 0.3 and 2.0 and most preferably between 0.7 and 1.7.

The part of the discharged gaseous $NH_3$ which is liquefied can also be expressed in relation to the quantity of removed $CO_2$. The quantity by weight of discharged gaseous $NH_3$ which is liquefied divided by the quantity by weight of removed $CO_2$ is preferably between 0,01 and 5, more preferably between 0.1 and 2.0 and most preferably between 0.5 and 1.5.

The absorption section may be of any known design, such as for example a trayed column so configured that the formed ammonium carbamate solution and the formed flow of gaseous $NH_3$ can be discharged separately.

In order to form the ammonium carbamate solution in the absorption section it is generally necessary to withdraw heat from the mixture. Therefore, prior to being fed to the absorption section, it is preferred to subject the mixture to a third cooling step, wherein partial condensation takes place whereby a liquid phase and a gas phase are formed. The liquid phase then consists essentially of an ammonium carbamate solution. In a further preferred embodiment the liquid phase is separated from the mixture. It is then possible to remove this liquid phase separately from the ammonium carbamate solution coming from the absorption section or to wholly or partially return it to the first cooling step. An advantage of the performance of the said third cooling step is that the operation of this step appears to be a control tool in determining the quantity of gaseous $NH_3$ that is released from the absorption section as a consequence of the fact that not all compounds of the mixture condense proprotionately; particularly $H_2O$ condenses preferentially, which makes it easier to separate gaseous $NH_3$ in the absorption section.

In another preferred embodiment of the process according to the invention a compression step is carried out on least the part of the discharged gaseous $NH_3$ that needs to be liquefied in the second cooling step. This presents the advantage that the condensation temperature of the gaseous $NH_3$ rises, which simplifies condensation. Preferably the gaseous $NH_3$ pressure is increased to at least 1.5 MPa, more preferably 1.8 MPa or even higher, for example 2 MPa or more. This presents the advantage that the condensation temperature of $NH_3$ at the stated pressures exceeds the temperature level at which plant cooling water circuits usually operate. This preferred embodiment can readily be combined with the aforesaid preferred embodiments such as the application of partial condensation.

The ammonium carbamate solution being formed in the absorption section has an amount of $NH_3$ and $NH_3$-derived compounds such as ammonium ions, and an amount of $CO_2$ and $CO_2$-derived compounds such as carbamate- or carbonate ions. The weight ratio between these two amounts is expressed as the N/C ratio of the ammonium carbamate solution. In a further embodiment of the process according to the invention, the N/C ratio in the ammonium carbamate solution is reduced to 1.4 or less by returning a part of the discharged ammonium carbamate solution to the first cooling step and by subjecting the gaseous $NH_3$ and/or the mixture to a second, respectively third cooling step. Preferably, the N/C ration is reduced to 1.3 or less, more preferably to 1.25 or less, most preferably to 1.2 or less. In this embodiment, it is preferred that the third cooling step comprises a partial condensation step on the mixture as describer above, prior to the mixture being fed to the absorption section, with a liquid phase and a gas phase being formed. Preferably, the liquid phase is subsequently separated from the mixture. Advantageously, a part of the discharged gaseous $NH_3$ is liquefied in the second step and returned to the absorption section, as described above. Here, it is preferred as described above that a compression step is carried out on at least the part of the discharged gaseous $NH_3$ that is to be liquefied.

BRIEF DESCRIPTION OF THE DRAWINGS

The process according to the invention is elucidated on the basis of the following drawings.

In the drawings

The first digit of the numbers in the figures is the same as the number of the figure. Where the last two digits of the numbers of different figures are the same, they refer to the same item.

DETAILED DESCRIPTION OF THE PREFERRED EMBODIMENTS

Figure 1:
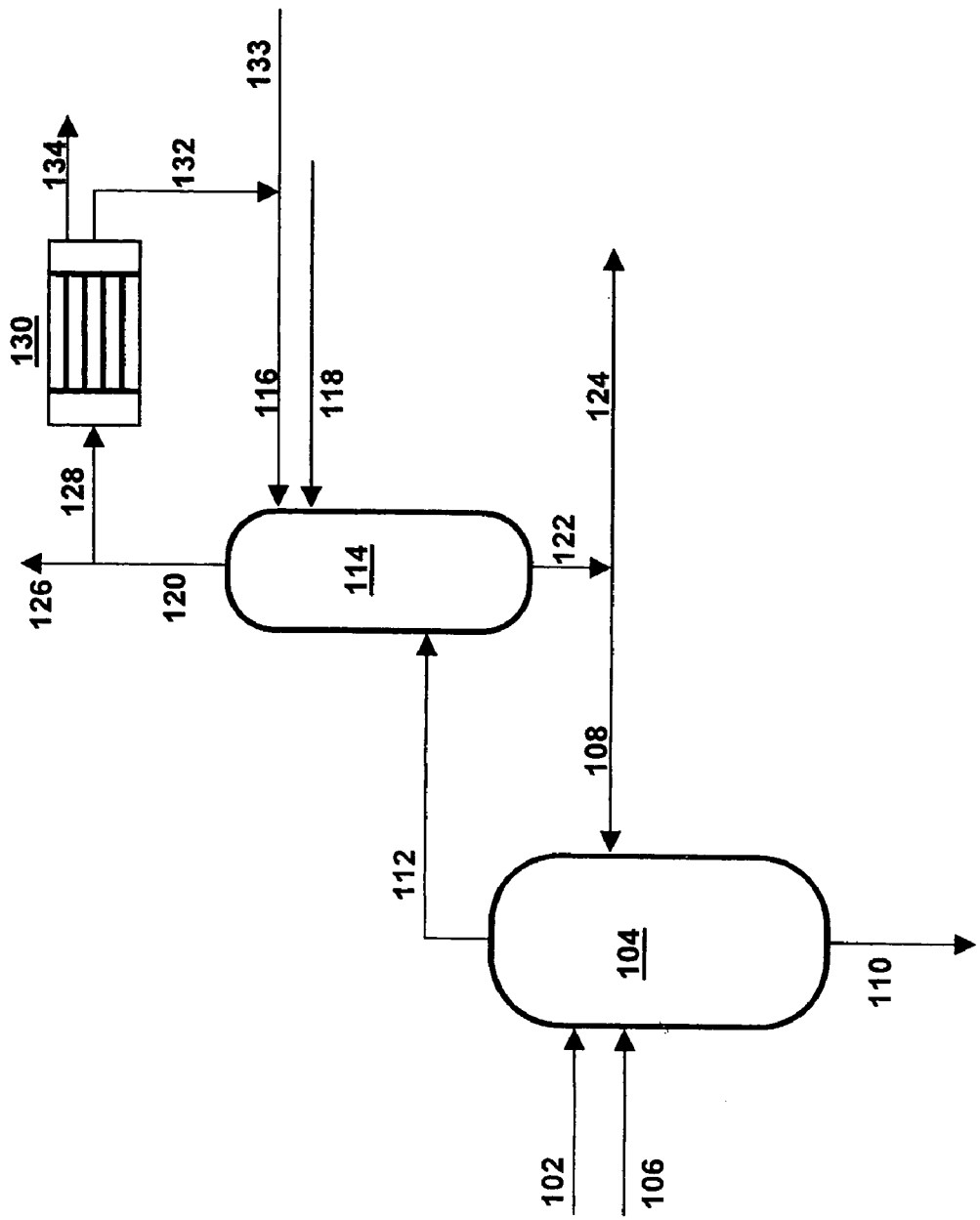
FIG. 1 shows an embodiment with a cooling vessel in which the first cooling step is carried out, an absorption section consisting of an absorber, a condenser wherein the gaseous $NH_3$ is liquefied in the second cooling step and wherein the gaseous $NH_3$ and the ammonium carbamate solution are returned to the absorber and the cooling vessel, respectively.

In FIG. 1 a gaseous flow coming from a melamine synthesis reactor is fed via line 102 to cooling vessel 104 and cooled with a coolant consisting of an aqueous flow supplied via line 106 and an ammonium carbamate solution, to be discussed later, which is supplied via line 108. During cooling there are formed a melamine slurry, which is discharged via line 110, and a gaseous mixture containing $NH_3$, $CO_2$ and $H_2O$, which is discharged via line 112 to absorber 114. Absorber 114 is supplied with a flow of liquid $NH_3$ via line 116 as well as an auxiliary flow, consisting essentially of water, via line 118. It is possible to combine lines 116 and 118 into one line. Contacting the mixture with the liquid $NH_3$ and the auxiliary flow results in the formation of a flow of gaseous $NH_3$, which is discharged via line 120, and an ammonium carbamate solution, which is discharged via line 122. The ammonium carbamate solution discharged via line 122 is split: one part is removed via line 124, the other part is returned via line 108 to cooling vessel 104. The gaseous $NH_3$ discharged via line 120 is split: one part is removed via line 126 and generally used as fluidization gas and/or atomizing gas for the melamine synthesis reactor, the other part is supplied via line 128 to condenser 130. In condenser 130 the $NH_3$ is liquefied and added via line 132 to liquid $NH_3$ supplied via line 133, after which the liquid $NH_3$ is fed to absorber 114. The compounds that are not liquefied in condenser 130, such as $N_2$ and $H_2$, as well as a small quantity of $NH_3$, are discharged as an inert vent stream via line 134.

Figure 2:
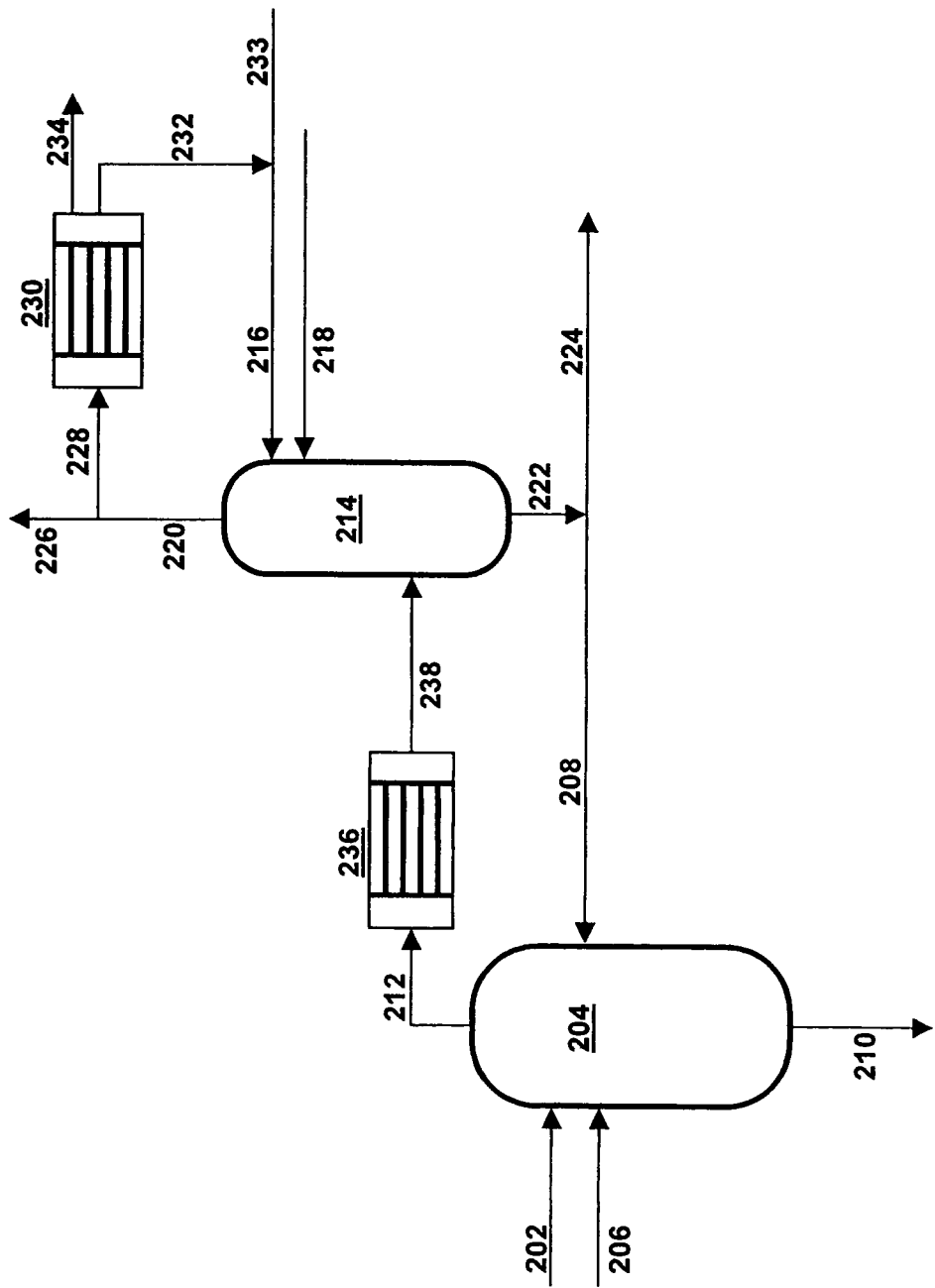
FIG. 2 shows an embodiment wherein, in comparison with the embodiment of FIG. 1, the mixture from the first cooling step is first passed through a condenser, where the third cooling step is executed, before being fed to the absorber.

In FIG. 2, in comparison with the embodiment of FIG. 1, the gaseous mixture containing $NH_3$, $CO_2$ and $H_2O$, which is discharged via line 212 from the cooling vessel 204, is fed to condenser 236. In condenser 236 partial condensation takes place so that a liquid phase and a gas phase are formed. The liquid phase and the gas phase are fed via line 238 to absorber 214.

Figure 3:
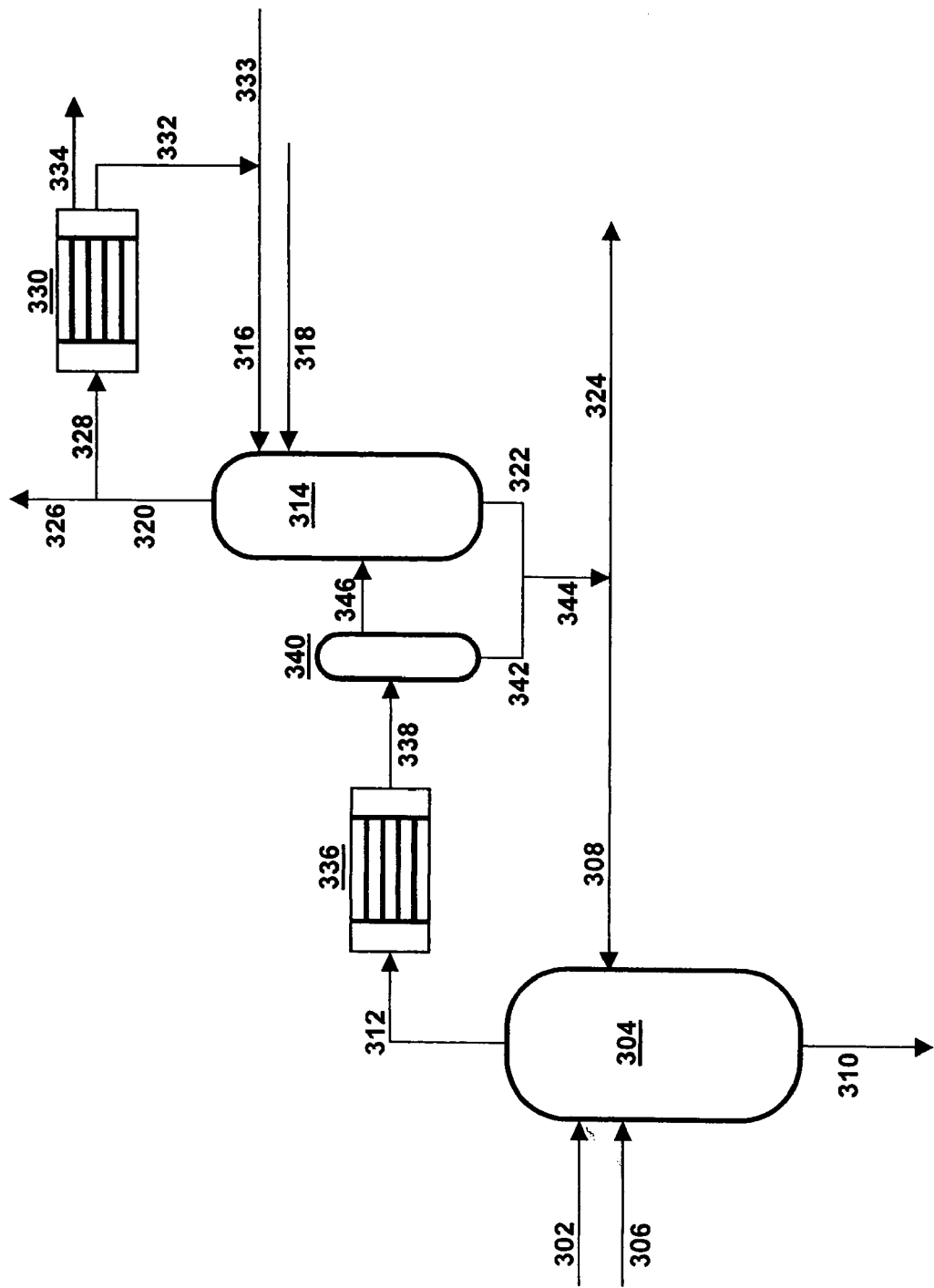
FIG. 3 shows an embodiment wherein, in comparison with the embodiment of FIG. 2, the liquid phase is separated from the flow coming from the condenser placed between cooling vessel and absorber and is added to the ammonium carbamate solution coming from the absorber.

In FIG. 3, in comparison with FIG. 2, a separator 340 is inserted between the condenser 336 and absorber 314. The liquid phase and the gas phase formed through partial condensation in condenser 336 are fed via line 338 to separator 340. The liquid phase is discharged via line 342 and combined with the ammonium carbamate solution discharged from absorber 314 via line 322. The combined flow is then discharged via line 344, after which the flow is split into a part that is fed to the cooling vessel and a part that is removed. The gas phase coming from the separator is fed to absorber 314 via line 346.

Figure 4:
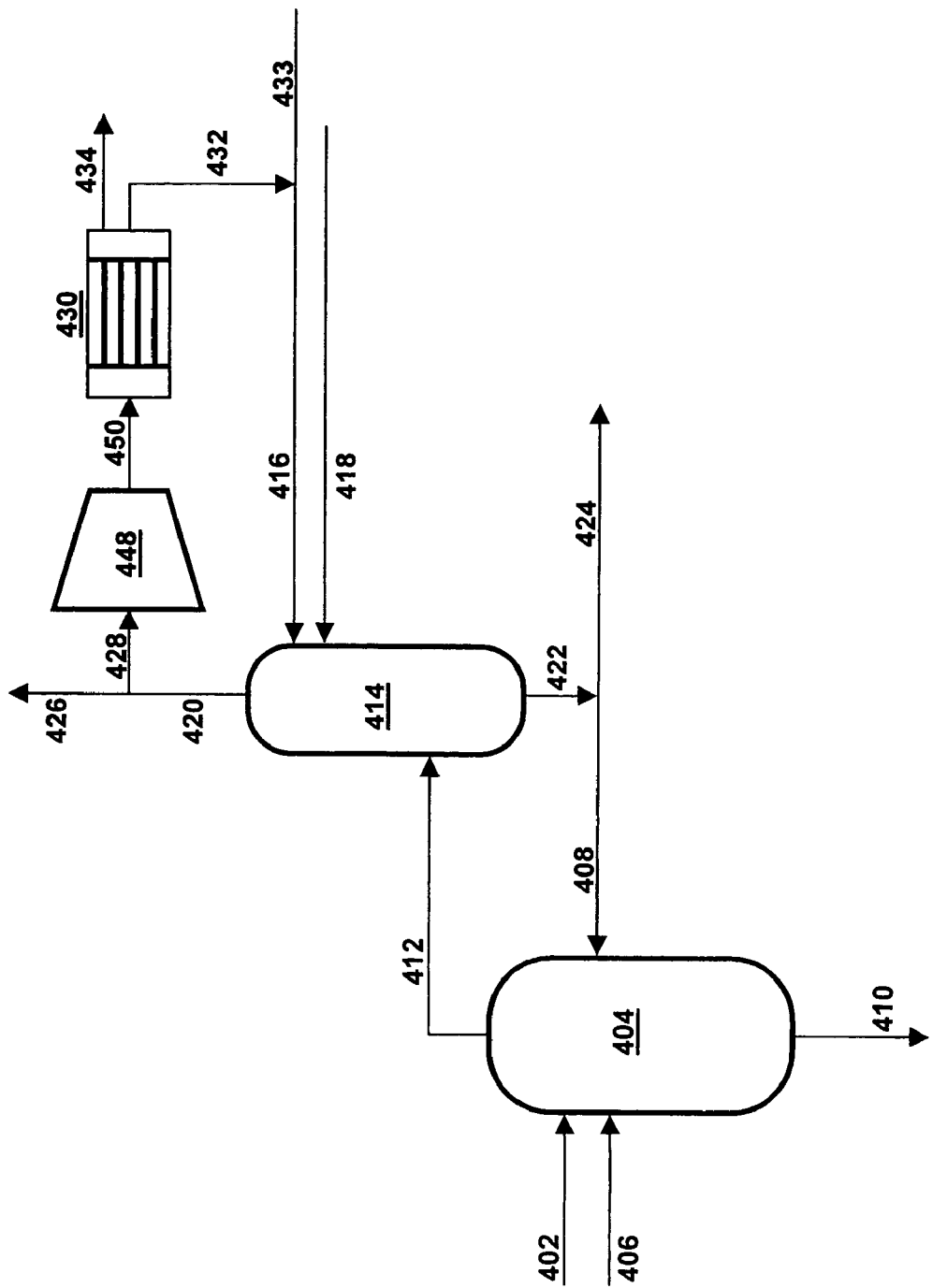
FIG. 4 shows an embodiment wherein, in comparison with the embodiment of FIG. 1, the part of the flow of gaseous $NH_3$ from the absorber that needs to be liquefied is compressed in a compressor, prior to the liquefaction in the second cooling step.

In FIG. 4, in comparison with FIG. 1, the part of the discharged flow of gaseous $NH_3$ to be liquefied is fed via line 428 to compressor 448. The flow of compressed gaseous $NH_3$ is subsequently fed via line 450 to condenser 430, where it is liquefied. The increased pressure makes it easier to liquefy the $NH_3$, since the condensation temperature of $NH_3$ increases when the pressure is increased.

Figure 5:
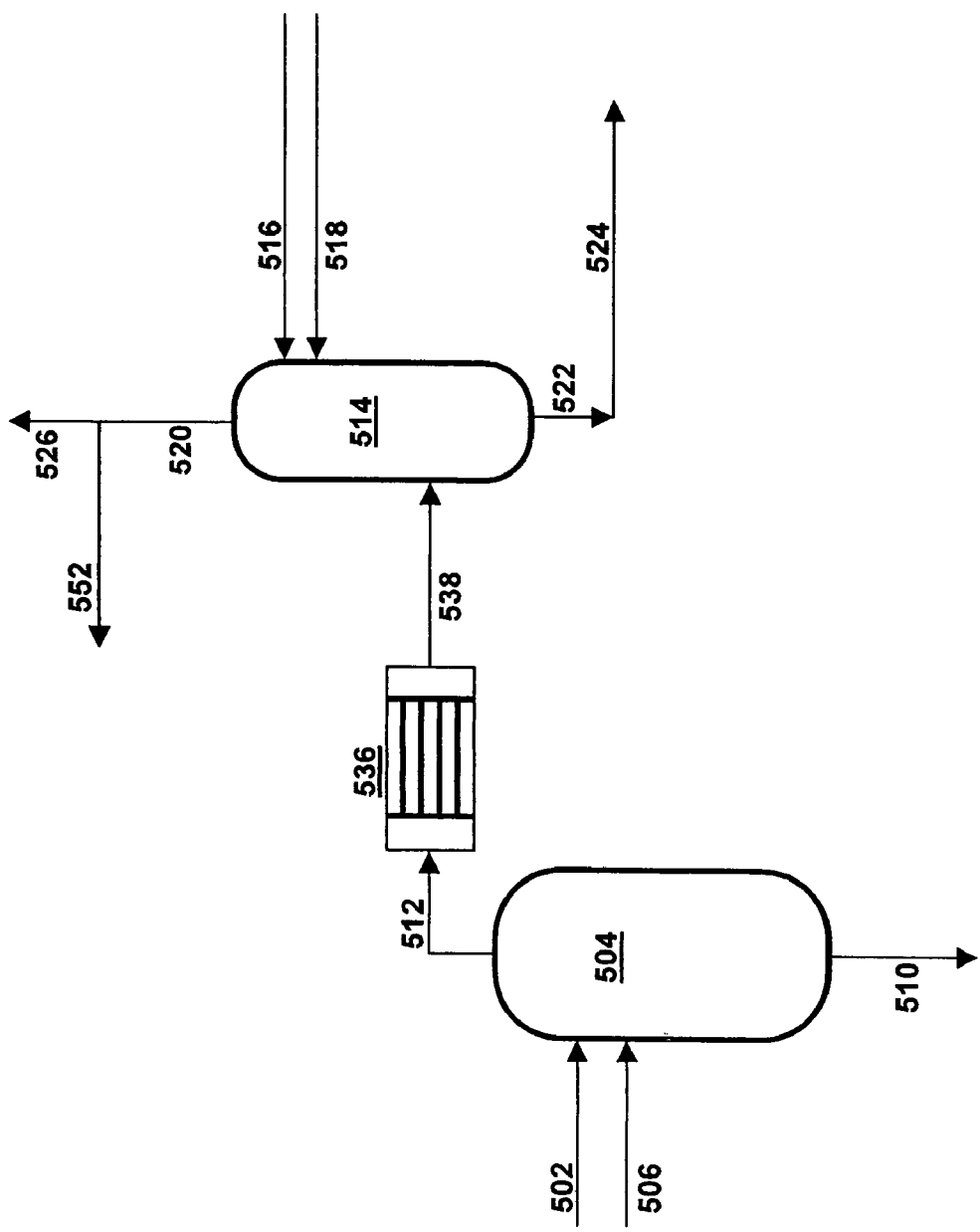
FIG. 5 shows an embodiment according to the state of the art.

FIG. 5 shows the state of the art without the presence of any means of liquefying a part of the flow of gaseous $NH_3$ and returning it to the absorber, and without any means of returning a part of the ammonium carbamate solution coming from the absorber to the cooling vessel. In addition a part of the flow of gaseous $NH_3$ discharged from absorber 514 via line 520 is discharged via line 552 to a scrubber unit in order to separate the inert compounds.

EXAMPLES

The process according to the invention is elucidated further on the basis of an example and a comparative experiment. The example has been conducted according to the embodiment described in FIG. 2. The comparative experiment has been conducted according to the embodiment of FIG. 5. See Table 1 and Table 2 for the results. In the tables ammonium carbamate is not represented as such but as converted quantities of $CO_2$ and $NH_3$.

The results indicate that, with melamine-containing gaseous feed streams of equal quantity and composition (via 202 and 502) and with virtually equal quantities of removed $CO_2$ (via 224 and 524) and removed gaseous $NH_3$ (via 226 and 526), the quantity of $NH_3$ that is discharged per unit time via the ammonium carbamate solution (via 224 and 524) is significantly smaller in the example than in the comparative experiment (7 tonnes/hour and 9 tonnes/hour, respectively). As a result, steam consumption in downstream steps for liberating $NH_3$ from the removed ammonium carbamate solution drops from 15 tonnes/hour steam for the ammonium carbamate solution removed via 524, to 12 tonnes/hour for the ammonium carbamate solution removed via 224.

In addition the quantity of $H_2O$ that is removed (via 224 and 524 respectively) is significantly lower in the example than in the comparative experiment (8.6 tonnes/hour and 13 tonnes/hour, respectively); this allows energy savings in utilizing the discharged $CO_2$ and $NH_3$ (for example for the synthesis of urea).

Also the required quantity of liquid $NH_3$ that needs to be supplied in the example via 233 is significantly lower than the quantity of liquid $NH_3$ that needs to be supplied in the comparative experiment via 516 (3 tonnes/hour and 9 tonnes/hour, respectively).

Furthermore, the inert vent stream according to the invention which is discharged via 234 and which in this example contains between 0.001 and 0.1 tonne/hour inert compounds such as $N_2$ and $H_2$, contains only little $NH_3$ (0.02 tonne/hour) so that separating the inert compounds is accomplished much more easily in comparison with the treatment which is necessary in the comparative experiment for the flow that is discharged via line 552, which flow in relation to the quantity of inert compounds, which also in this comparative experiment is between 0.001 and 0.1 tonne/hour, contains very much $NH_3$ (5 tonnes/hour).

The results also indicate that the N/C ratio in the ammonium carbamate stream discharged from the absorption section according to the invention via 222 is 10/8, i.e. 1.25, which is significantly lower than the N/C ratio of the ammonium carbamate stream discharged from the absorption section in the comparative experiment via 522, which is 9/6, i.e. 1.5.

TABLE 1

Results of the comparative experiment (see FIG. 5)

| | Flow | | | | | | | | | | | |
|---|---|---|---|---|---|---|---|---|---|---|---|---|
| | 502 | 506 | 510 | 512 | 516 | 518 | 520 | 522 | 524 | 526 | 538 | 552 |
| Melamine | 5 | 0 | 5 | 0 | 0 | 0 | 0 | 0 | 0 | 0 | 0 | 0 |
| $NH_3$ | 28 | 0.9 | 0.9 | 28 | 9 | 0 | 28 | 9 | 9 | 23 | 28 | 5 |
| $CO_2$ | 6 | 0.3 | 0.3 | 6 | 0 | 0 | 0 | 6 | 6 | 0 | 6 | 0 |
| $H_2O$ | 0 | 19 | 6 | 13 | 0 | 0.6 | 0.002 | 13.6 | 13.6 | 0.002 | 13 | 0 |
| Total [tonnes/h] | 39 | 20.2 | 12.2 | 47 | 9 | 0.6 | 28 | 28.6 | 28.6 | 23 | 47 | 5 |
| T [° C.] | 400 | 80 | 117 | 117 | 15 | 15 | 6 | 80 | 80 | 6 | 80 | 6 |
| P [MPa] | 0.6 | | 0.6 | 0.6 | 1.6 | 1.6 | 0.5 | 0.5 | 0.5 | 0.5 | 0.5 | 0.5 |
| Wt % gas | 100 | 0 | 0 | 100 | 0 | 0 | 100 | 0 | 0 | 100 | 49 | 100 |

TABLE 2

Results of the example (see FIG. 2)

| | Flow | | | | | | | | | | | | | |
|---|---|---|---|---|---|---|---|---|---|---|---|---|---|---|
| | 202 | 206 | 208 | 210 | 212 | 216 | 218 | 220 | 222 | 224 | 226 | 228 | 233 | 234 | 238 |
| Melamine | 5 | 0 | 0 | 5 | 0 | 0 | 0 | 0 | 0 | 0 | 0 | 0 | 0 | 0 | 0 |
| $NH_3$ | 28 | 1 | 3 | 2 | 30 | 8 | 0 | 28 | 10 | 7 | 23 | 5 | 3 | 0.02 | 30 |
| $CO_2$ | 6 | 1 | 2 | 1 | 8 | 0 | 0 | 0 | 8 | 6 | 0 | 0 | 0 | 0 | 8 |
| $H_2O$ | 0 | 14 | 3 | 6 | 11 | 0 | 0.6 | 0.003 | 11.6 | 8.6 | 0.003 | 0 | 0.6 | 0 | 11 |
| Total [tonnes/h] | 39 | 16 | 8 | 14 | 49 | 8 | 0.6 | 28 | 29.6 | 21.6 | 23 | 5 | 3.6 | 0.02 | 49 |
| T [° C.] | 400 | 80 | 74 | 112 | 112 | 29 | 29 | 7 | 74 | 74 | 7 | 7 | 21 | | 77 |
| P [MPa] | 0.6 | | 0.5 | 0.6 | 0.6 | 1.6 | 1.6 | 0.5 | 0.5 | 0.5 | 0.5 | 0.5 | 1.6 | | 0.5 |
| Wt % gas | 100 | 0 | 0 | 0 | 100 | 0 | 0 | 100 | 0 | 0 | 100 | 100 | 0 | 100 | 48 |

Note:
If $NH_3$, $CO_2$ and $H_2O$ are all present in a flow that consists of less than 100 wt % gas, said compounds are at least partly present in the form of an ammonium carbamate solution.

The invention claimed is:

1. Process for preparing melamine, comprising the steps of:

(a) cooling in a first cooling step a melamine synthesis gas to form a melamine slurry and a gaseous mixture containing $NH_3$, $CO_2$ and $H_2O$;

(b) feeding the gaseous mixture and a flow of liquid $NH_3$ to an absorption section;

(c) contacting the mixture and the flow of liquid $NH_3$ in the absorption section with each other to form therein gaseous $NH_3$ and an ammonium carbamate solution;

(d) separately discharging a stream of the gaseous $NH_3$ and a stream of the ammonium carbamate solution from the absorption section, (e) returning one part of the discharged stream of ammonium carbamate solution to the first cooling step;

(f) removing from the process a second part of the discharged stream of ammonium carbamate solution, wherein the removed second part of the discharged stream of ammonium carbamate solution comprises $CO_2$ which is thereby removed from the process;

(g) liquefying in a second cooling step a part of the stream of gaseous $NH_3$ which is discharged from the absorption section according to step (d); and (h) returning to the absorption section the liquefied $NH_3$ obtained in the second cooling step according to step (g), wherein the quantity by weight of the gaseous $NH_3$ which is discharged from the absorption section according to step (d) and is liquefied in the second cooling step according to step (g) divided by the quantity by weight of the $CO_2$ removed from the process by the second part of the discharged ammonium carbamate solution according to step (f) is between 0.01 and 5.

2. Process according to claim 1, wherein prior to feeding the mixture to the absorption section according to step (b), the process further comprises cooling the mixture in a third cooling step to thereby cause partial condensation to take place and thereby form a liquid phase and gas phase.

3. Process according to claim 2, further comprising separating the liquid phase from the gas phase.

4. Process according to claim 1, further comprising compressing in a compression step at least the part of the discharged gaseous $NH_3$ that is to be liquefied.

5. Process for preparing melamine, comprising the steps of:
  (a) cooling in a first cooling step a melamine synthesis gas to form a melamine slurry and a gaseous mixture containing $NH_3$, $CO_2$ and $H_2O$;
  (b) feeding the gaseous mixture and a flow of liquid $NH_3$ to an absorption section;
  (c) contacting the mixture and the flow of liquid $NH_3$ in the absorption section with each other to form therein gaseous $NH_3$ and an ammonium carbamate solution;
  (d) separately discharging a stream of the gaseous $NH_3$ and a stream of the ammonium carbamate solution from the absorption section, and
  (e) reducing the N/C ratio in the ammonium carbamate solution to 1.4 or less by (e1) returning to the first cooling step a first part of the stream of ammonium carbamate solution which is discharged from the absorption section according to step (d) while removing from the process a second part of the stream of ammonium carbamate solution which is discharged from the absorption section according to step (d), and (e2) subjecting the gaseous $NH_3$ and/or the mixture to a second, respectively third, cooling step.

6. Process according to claim 5, wherein the N/C ratio is reduced to 1.3 or less.

7. Process according to claim 5, wherein the N/C ratio is reduced to 1.2 or less.

8. Process according to claim 5, wherein the third cooling step comprises a partial condensation step on the mixture, prior to the mixture being fed to the absorption section, with a liquid phase and a gas phase being formed.

9. Process according to claim 8, further comprising separating the liquid phase from the mixture.

10. Process according to claim 5, wherein a part of the discharged gaseous $NH_3$ is liquefied in the second cooling step and returned to the absorption section.

11. Process according to claim 10, further comprising compressing in a compression step at least the part of the discharged gaseous $NH_3$ that is to be liquefied in the second cooling step.

12. Process according to claim 8, wherein a part of the discharged gaseous $NH_3$ is liquefied in the second cooling step and returned to the absorption section.

13. Process according to claim 12, further comprising compressing in a compression step at least the part of the discharged gaseous $NH_3$ that is to be liquefied in the second cooling step.

* * * * *